(12) United States Patent
Willyard et al.

(10) Patent No.: US 8,894,640 B2
(45) Date of Patent: Nov. 25, 2014

(54) OPTICAL DETECTION OF INTERRUPTED FLUID FLOW TO ABLATION PROBE

(71) Applicant: Vivant Medical, Inc., Boulder, CO (US)

(72) Inventors: Richard A. Willyard, Longmont, CO (US); Joseph D. Brannan, Erie, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/791,262

(22) Filed: Mar. 8, 2013

(65) Prior Publication Data

US 2013/0190749 A1     Jul. 25, 2013

Related U.S. Application Data

(62) Division of application No. 12/566,299, filed on Sep. 24, 2009, now Pat. No. 8,394,087.

(51) Int. Cl.
    *A61B 18/18*      (2006.01)
    *A61B 18/12*      (2006.01)
    *A61B 18/00*      (2006.01)

(52) U.S. Cl.
    CPC .......... *A61B 18/1815* (2013.01); *A61B 18/1206* (2013.01); *A61B 2018/00011* (2013.01); *A61B 18/1233* (2013.01)
    USPC .............................................. 606/34; 606/41

(58) Field of Classification Search
    USPC .................... 606/34, 41; 607/98, 100, 101
    See application file for complete search history.

(56) References Cited

U.S. PATENT DOCUMENTS

| | | | |
|---|---|---|---|
| D223,367 S | | 4/1972 | Kountz |
| 4,126,132 A | * | 11/1978 | Portner et al. ............... 604/123 |
| 4,137,913 A | * | 2/1979 | Georgi ............................ 604/67 |
| D263,020 S | | 2/1982 | Rau, III |
| D266,842 S | | 11/1982 | Villers et al. |
| D278,306 S | | 4/1985 | McIntosh |
| 4,559,454 A | * | 12/1985 | Kramer ......................... 250/577 |
| D295,893 S | | 5/1988 | Sharkany et al. |
| D295,894 S | | 5/1988 | Sharkany et al. |

(Continued)

FOREIGN PATENT DOCUMENTS

| | | |
|---|---|---|
| CN | 1103807 | 6/1995 |
| DE | 390937 | 3/1924 |

(Continued)

OTHER PUBLICATIONS

U.S. Appl. No. 08/136,098, filed Oct. 14, 1993, Roger A. Stern.

(Continued)

*Primary Examiner* — Linda Dvorak
*Assistant Examiner* — Jocelyn D Ram (57) ABSTRACT

An electrosurgical system includes an electrosurgical device adapted to direct energy to tissue and a fluid path leading to the electrosurgical device. The system also includes an optical sensor unit operably associated with the fluid path. The optical sensor unit includes a light-emitting element to generate light output and a light-receiving element to collect light outputted from the light-emitting element. The light-emitting element and the light-receiving element are disposed such that light output from the light-emitting element passes through the fluid path to the light-receiving element. The optical sensor unit is capable of detecting an air bubble in the fluid path passing through the optical sensor unit using a sensed characteristic of light collected at the light-receiving element.

10 Claims, 4 Drawing Sheets

(56) References Cited

U.S. PATENT DOCUMENTS

| | | | |
|---|---|---|---|
| 4,891,483 A | 1/1990 | Kikuchi et al. | |
| 5,006,110 A * | 4/1991 | Garrison et al. | 604/65 |
| 5,072,595 A * | 12/1991 | Barbier | 62/129 |
| 5,129,396 A | 7/1992 | Rosen et al. | |
| D354,218 S | 1/1995 | Van de Peer | |
| 5,697,927 A | 12/1997 | Imran et al. | |
| 6,007,571 A | 12/1999 | Neilson et al. | |
| D424,693 S | 5/2000 | Pruter | |
| D424,694 S | 5/2000 | Tetzlaff et al. | |
| D425,201 S | 5/2000 | Tetzlaff et al. | |
| 6,223,085 B1 | 4/2001 | Dann et al. | |
| 6,226,080 B1 | 5/2001 | Takeuchi et al. | |
| D449,886 S | 10/2001 | Tetzlaff et al. | |
| 6,355,024 B1 | 3/2002 | Small et al. | |
| D457,958 S | 5/2002 | Dycus et al. | |
| D457,959 S | 5/2002 | Tetzlaff et al. | |
| 6,451,015 B1 | 9/2002 | Rittman, III et al. | |
| 6,531,708 B1 * | 3/2003 | Malmstrom et al. | 250/573 |
| 6,575,969 B1 | 6/2003 | Rittman, III et al. | |
| D487,039 S | 2/2004 | Webster et al. | |
| 6,750,468 B2 * | 6/2004 | Malmstrom et al. | 250/573 |
| 6,752,767 B2 | 6/2004 | Turovskiy et al. | |
| D496,997 S | 10/2004 | Dycus et al. | |
| D499,181 S | 11/2004 | Dycus et al. | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| 7,161,313 B2 | 1/2007 | Piepgras et al. | |
| D541,418 S | 4/2007 | Schechter et al. | |
| D541,938 S | 5/2007 | Kerr et al | |
| 7,311,703 B2 | 12/2007 | Turovskiy et al. | |
| D564,662 S | 3/2008 | Moses et al. | |
| D576,932 S | 9/2008 | Strehler | |
| 7,468,042 B2 | 12/2008 | Turovskiy et al. | |
| D594,736 S | 6/2009 | Esjunin | |
| D594,737 S | 6/2009 | Kelly et al. | |
| D606,203 S | 12/2009 | Husheer et al. | |
| 7,642,451 B2 | 1/2010 | Bonn | |
| 7,661,293 B2 * | 2/2010 | Dam | 73/19.03 |
| 7,661,294 B2 * | 2/2010 | Dam | 73/19.03 |
| D613,412 S | 4/2010 | DeCarlo | |
| 7,818,992 B2 * | 10/2010 | Riley et al. | 73/19.03 |
| 7,846,108 B2 | 12/2010 | Turovskiy et al. | |
| 7,875,024 B2 | 1/2011 | Turovskiy et al. | |
| D634,010 S | 3/2011 | DeCarlo | |
| 8,035,570 B2 | 10/2011 | Prakash et al. | |
| 8,059,059 B2 | 11/2011 | Bonn | |
| 8,082,112 B2 * | 12/2011 | Butterfield et al. | 702/25 |
| 8,104,348 B2 * | 1/2012 | Balschat et al. | 73/599 |
| 8,118,808 B2 | 2/2012 | Smith et al. | |
| 8,182,480 B2 | 5/2012 | Huseman | |
| 8,192,427 B2 | 6/2012 | Buysse | |
| 8,197,473 B2 | 6/2012 | Rossetto et al. | |
| 8,202,270 B2 | 6/2012 | Rossetto et al. | |
| 8,211,098 B2 | 7/2012 | Paulus | |
| 8,211,099 B2 | 7/2012 | Buysse et al. | |
| 8,216,227 B2 | 7/2012 | Podhajsky | |
| 8,221,418 B2 | 7/2012 | Prakash et al. | |
| 8,235,981 B2 | 8/2012 | Prakash et al. | |
| 8,394,087 B2 | 3/2013 | Willyard et al. | |
| 8,398,575 B1 * | 3/2013 | McCall | 604/4.01 |
| 8,419,709 B2 * | 4/2013 | Haddad et al. | 604/507 |
| 8,435,237 B2 | 5/2013 | Bahney | |
| 2002/0151884 A1 | 10/2002 | Hoey et al. | |
| 2003/0032951 A1 | 2/2003 | Rittman et al. | |
| 2005/0015081 A1 | 1/2005 | Turovskiy et al. | |
| 2005/0065584 A1 * | 3/2005 | Schiff et al. | 607/105 |
| 2005/0149010 A1 | 7/2005 | Turovskiy et al. | |
| 2005/0209563 A1 * | 9/2005 | Hopping et al. | 604/151 |
| 2005/0245920 A1 | 11/2005 | Vitullo et al. | |
| 2007/0142829 A1 | 6/2007 | Ahn et al. | |
| 2008/0161890 A1 | 7/2008 | Lafontaine | |
| 2008/0183165 A1 | 7/2008 | Buysse et al. | |
| 2008/0269851 A1 | 10/2008 | Deem et al. | |
| 2009/0138005 A1 | 5/2009 | Prakash et al. | |
| 2009/0149850 A1 | 6/2009 | Turovskiy et al. | |
| 2009/0163858 A1 * | 6/2009 | Haddad et al. | 604/67 |
| 2009/0183895 A1 | 7/2009 | Bonn | |
| 2009/0187180 A1 | 7/2009 | Brannan | |
| 2009/0192510 A1 | 7/2009 | Bahney | |
| 2009/0198226 A1 | 8/2009 | Prakash et al. | |
| 2009/0198227 A1 | 8/2009 | Prakash | |
| 2009/0222002 A1 | 9/2009 | Bonn et al. | |
| 2009/0248005 A1 | 10/2009 | Rusin et al. | |
| 2009/0248006 A1 | 10/2009 | Paulus et al. | |
| 2009/0264877 A1 | 10/2009 | DeCarlo | |
| 2009/0295674 A1 | 12/2009 | Bonn | |
| 2009/0306652 A1 | 12/2009 | Buysse et al. | |
| 2009/0306659 A1 | 12/2009 | Buysse | |
| 2009/0326620 A1 | 12/2009 | Rossetto et al. | |
| 2010/0030206 A1 | 2/2010 | Brannan et al. | |
| 2010/0030208 A1 | 2/2010 | Manley | |
| 2010/0030210 A1 | 2/2010 | Paulus | |
| 2010/0036379 A1 | 2/2010 | Prakash et al. | |
| 2010/0045558 A1 | 2/2010 | Rossetto | |
| 2010/0045559 A1 | 2/2010 | Rossetto | |
| 2010/0049185 A1 | 2/2010 | Paulus | |
| 2010/0049193 A1 | 2/2010 | Huseman | |
| 2010/0053015 A1 | 3/2010 | Willyard | |
| 2010/0057070 A1 | 3/2010 | Behnke et al. | |
| 2010/0076422 A1 | 3/2010 | Podhajsky | |
| 2010/0082082 A1 | 4/2010 | Prakash et al. | |
| 2010/0087808 A1 | 4/2010 | Paulus | |
| 2010/0094272 A1 | 4/2010 | Rossetto et al. | |
| 2010/0094273 A1 | 4/2010 | Rossetto et al. | |
| 2010/0097284 A1 | 4/2010 | Brannan et al. | |
| 2010/0217251 A1 | 8/2010 | Rossetto et al. | |
| 2010/0217252 A1 | 8/2010 | Rossetto et al. | |
| 2010/0234839 A1 | 9/2010 | Smith et al. | |
| 2010/0256624 A1 | 10/2010 | Brannan et al. | |
| 2010/0262134 A1 | 10/2010 | Jensen et al. | |
| 2010/0286681 A1 | 11/2010 | Podhajsky | |
| 2010/0286682 A1 | 11/2010 | Podhajsky | |
| 2010/0286683 A1 | 11/2010 | Podhajsky | |
| 2010/0305559 A1 | 12/2010 | Brannan et al. | |
| 2010/0305560 A1 | 12/2010 | Peterson | |
| 2010/0305561 A1 | 12/2010 | Prakash et al. | |
| 2011/0071511 A1 * | 3/2011 | Brannan et al. | 606/33 |
| 2011/0208177 A1 | 8/2011 | Brannan | |
| 2012/0016359 A1 | 1/2012 | Podhajsky | |
| 2012/0022622 A1 | 1/2012 | Johnson et al. | |

FOREIGN PATENT DOCUMENTS

| | | |
|---|---|---|
| DE | 390937 C | 3/1924 |
| DE | 1099658 | 2/1961 |
| DE | 1099658 B | 2/1961 |
| DE | 1139927 | 11/1962 |
| DE | 1139927 B | 11/1962 |
| DE | 1149832 | 6/1963 |
| DE | 1149832 B | 6/1963 |
| DE | 1439302 | 1/1969 |
| DE | 1439302 A1 | 1/1969 |
| DE | 2439587 | 2/1975 |
| DE | 2439587 A1 | 2/1975 |
| DE | 2455174 | 5/1975 |
| DE | 2455174 A1 | 5/1975 |
| DE | 2407559 | 8/1975 |
| DE | 2407559 A1 | 8/1975 |
| DE | 2415263 | 10/1975 |
| DE | 2415263 A1 | 10/1975 |
| DE | 2429021 | 1/1976 |
| DE | 2429021 A1 | 1/1976 |
| DE | 2460481 | 6/1976 |
| DE | 2460481 A1 | 6/1976 |
| DE | 2602517 | 7/1976 |
| DE | 2602517 A1 | 7/1976 |
| DE | 2504280 | 8/1976 |
| DE | 2504280 A1 | 8/1976 |
| DE | 2627679 | 1/1977 |
| DE | 2627679 A1 | 1/1977 |
| DE | 2540968 | 3/1977 |
| DE | 2540968 A1 | 3/1977 |

(56) References Cited

FOREIGN PATENT DOCUMENTS

| | | |
|---|---|---|
| DE | 2820908 | 11/1978 |
| DE | 2820908 A1 | 11/1978 |
| DE | 2803275 | 8/1979 |
| DE | 2803275 A1 | 8/1979 |
| DE | 2823291 | 11/1979 |
| DE | 2823291 A1 | 11/1979 |
| DE | 2946728 | 5/1981 |
| DE | 2946728 A1 | 5/1981 |
| DE | 3143421 | 5/1982 |
| DE | 3143421 A1 | 5/1982 |
| DE | 3045996 | 7/1982 |
| DE | 3045996 A1 | 7/1982 |
| DE | 3120102 | 12/1982 |
| DE | 3120102 A1 | 12/1982 |
| DE | 3510586 | 10/1986 |
| DE | 3510586 A1 | 10/1986 |
| DE | 3604823 | 8/1987 |
| DE | 3604823 A1 | 8/1987 |
| DE | 8712328 U1 | 2/1988 |
| DE | 8712328 | 3/1988 |
| DE | 3711511 | 6/1988 |
| DE | 3711511 C1 | 6/1988 |
| DE | 3904558 | 8/1990 |
| DE | 3904558 A1 | 8/1990 |
| DE | 3942998 | 7/1991 |
| DE | 3942998 A1 | 7/1991 |
| DE | 4238263 | 5/1993 |
| DE | 4238263 A1 | 5/1993 |
| DE | 4303882 | 8/1994 |
| DE | 04303882 C2 | 2/1995 |
| DE | 4339049 | 5/1995 |
| DE | 4339049 A1 | 5/1995 |
| DE | 29616210 U1 | 11/1996 |
| DE | 29616210 | 1/1997 |
| DE | 19608716 | 4/1997 |
| DE | 19608716 C1 | 4/1997 |
| DE | 19751106 | 5/1998 |
| DE | 19751106 A1 | 5/1998 |
| DE | 19717411 | 11/1998 |
| DE | 19717411 A1 | 11/1998 |
| DE | 19751108 | 5/1999 |
| DE | 19751108 A1 | 5/1999 |
| DE | 19801173 | 7/1999 |
| DE | 19801173 C1 | 7/1999 |
| DE | 19848540 | 5/2000 |
| DE | 19848540 A1 | 5/2000 |
| DE | 10224154 | 12/2003 |
| DE | 10224154 A1 | 12/2003 |
| DE | 10310765 | 9/2004 |
| DE | 10328514 | 3/2005 |
| DE | 10328514 B3 | 3/2005 |
| DE | 102004022206 | 12/2005 |
| DE | 102004022206 A1 | 12/2005 |
| DE | 202005015147 U1 | 2/2006 |
| DE | 202005015147 | 3/2006 |
| DE | 102009015699 | 5/2010 |
| EP | 0 246 350 | 11/1987 |
| EP | 0 246 350 A1 | 11/1987 |
| EP | 0 481 685 | 4/1992 |
| EP | 0 481 685 A1 | 4/1992 |
| EP | 0 521 264 | 1/1993 |
| EP | 0 521 264 A2 | 1/1993 |
| EP | 0 541 930 | 5/1993 |
| EP | 0 556 705 | 8/1993 |
| EP | 0 556 705 A1 | 8/1993 |
| EP | 0 558 429 | 9/1993 |
| EP | 0 558 429 A1 | 9/1993 |
| EP | 0 572 131 | 12/1993 |
| EP | 0572131 A1 | 12/1993 |
| EP | 0541930 B1 | 3/1998 |
| EP | 0 836 868 | 4/1998 |
| EP | 0 836 868 A2 | 4/1998 |
| EP | 0 882 955 | 12/1998 |
| EP | 1 159 926 | 5/2001 |
| EP | 1 159 926 A2 | 12/2001 |
| EP | 0 648 515 | 4/2003 |
| EP | 1506757 | 2/2005 |
| EP | 1506757 A1 | 2/2005 |
| EP | 1 905 375 A1 | 4/2008 |
| EP | 1905375 | 4/2008 |
| EP | 2098184 | 9/2009 |
| EP | 2098184 A1 | 9/2009 |
| EP | 2158868 | 3/2010 |
| EP | 2158868 A1 | 3/2010 |
| EP | 2255742 | 12/2010 |
| EP | 2255742 A1 | 12/2010 |
| EP | 2322113 | 5/2011 |
| EP | 2322113 A1 | 5/2011 |
| EP | 2399646 | 12/2011 |
| EP | 2399646 A1 | 12/2011 |
| FR | 179 607 | 11/1906 |
| FR | 179607 | 11/1906 |
| FR | 1275 415 | 9/1960 |
| FR | 1 275 415 | 10/1961 |
| FR | 1 275 415 A | 11/1961 |
| FR | 1 347 865 | 11/1963 |
| FR | 1 347 865 A | 1/1964 |
| FR | 2 276 027 | 6/1974 |
| FR | 2 235 669 | 1/1975 |
| FR | 2 235 669 A1 | 1/1975 |
| FR | 2 276 027 | 1/1976 |
| FR | 2 276 027 A1 | 1/1976 |
| FR | 2 313 708 | 12/1976 |
| FR | 2 313 708 A1 | 12/1976 |
| FR | 2 502 935 | 10/1982 |
| FR | 2 502 935 A1 | 10/1982 |
| FR | 2 517 953 | 6/1983 |
| FR | 2 517 953 A1 | 6/1983 |
| FR | 2 573 301 | 11/1984 |
| FR | 2 573 301 | 5/1986 |
| FR | 2 573 301 A1 | 5/1986 |
| FR | 2 862 813 | 5/2005 |
| FR | 2 862 813 A1 | 5/2005 |
| FR | 2 864 439 | 7/2005 |
| FR | 2 864 439 A1 | 7/2005 |
| GB | 2 403 148 | 12/2004 |
| GB | 2403148 A | 12/2004 |
| JP | 5-5106 | 1/1993 |
| JP | 05-40112 | 2/1993 |
| JP | 06343644 | 12/1994 |
| JP | 06343644 A | 12/1994 |
| JP | 07265328 | 10/1995 |
| JP | 07265328 A | 10/1995 |
| JP | 08056955 | 3/1996 |
| JP | 08056955 A | 3/1996 |
| JP | 08252263 | 10/1996 |
| JP | 08252263 A | 10/1996 |
| JP | 09000492 | 1/1997 |
| JP | 09010223 | 1/1997 |
| JP | 09010223 A | 1/1997 |
| JP | 11244298 | 9/1999 |
| JP | 11244298 A | 9/1999 |
| JP | 2000342599 | 12/2000 |
| JP | 2000342599 A | 12/2000 |
| JP | 2000350732 | 12/2000 |
| JP | 2000350732 A | 12/2000 |
| JP | 2001003776 | 1/2001 |
| JP | 2001008944 | 1/2001 |
| JP | 2001008944 A | 1/2001 |
| JP | 2001029356 | 2/2001 |
| JP | 2001029356 A | 2/2001 |
| JP | 2001037775 | 2/2001 |
| JP | 2601029356 | 2/2001 |
| JP | 2001128990 | 5/2001 |
| JP | 2001128990 A | 5/2001 |
| JP | 2001231870 | 8/2001 |
| JP | 2008142467 | 6/2008 |
| SU | 166452 | 11/1964 |
| SU | 401367 A1 | 10/1973 |
| SU | 401367 | 11/1974 |
| SU | 727201 | 4/1980 |
| SU | 727201 A2 | 4/1980 |
| WO | 00/36985 A2 | 6/2000 |
| WO | 0036985 | 6/2000 |

(56) References Cited

FOREIGN PATENT DOCUMENTS

| | | |
|---|---|---|
| WO | WO00/36985 | 6/2000 |
| WO | WO03/088806 | 10/2003 |
| WO | 2007/006158 | 1/2007 |
| WO | 20071006158 A1 | 1/2007 |
| WO | WO2010/035831 | 4/2010 |
| WO | 2011/063061 | 5/2011 |
| WO | 2011063061 A2 | 5/2011 |

OTHER PUBLICATIONS

U.S. Appl. No. 08/483,742, filed Jun. 7, 1995, Roger A. Stern.
U.S. Appl. No. 13/236,997, filed Sep. 20, 2011, Behnke II, et al.
U.S. Appl. No. 13/237,068, filed Sep. 20, 2011, Behnke II, et al.
U.S. Appl. No. 13/237,187, filed Sep. 20, 2011, Behnke II, et al.
U.S. Appl. No. 13/237,342, filed Sep. 20, 2011, Behnke II, et al.
U.S. Appl. No. 13/237,488, filed Sep. 20, 2011, Behnke II, et al.
U.S. Appl. No. 13/343,788, filed Jan. 5, 2012, William O. Reid Jr.
U.S. Appl. No. 13/343,798, filed Jan. 5, 2012, William O. Reid Jr.
U.S. Appl. No. 13/344,753, filed Jan. 6, 2012, Lee et al.
U.S. Appl. No. 13/344,790, filed Jan. 6, 2012, Lee et al.
U.S. Appl. No. 13/358,129, filed Jan. 25, 2012, Brannan.
U.S. Appl. No. 13/400,223, filed Feb. 20, 2012, Anthony B. Ross.
U.S. Appl. No. 13/419,981, filed Mar. 14, 2012, Joseph D. Brannan.
U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,320, filed May 22, 2012, Joseph D. Brannan.
U.S. Appl. No. 13/657,270, filed Oct. 22, 2012, Brannan.
U.S. Appl. No. 13/657,609, filed Oct. 22, 2012, Prakash.
U.S. Appl. No. 13/657,638, filed Oct. 22, 2012, Brannan.
U.S. Appl. No. 13/681,741, filed Nov. 20, 2012, Steven Kim.
U.S. Appl. No. 13/711,067, filed Dec. 11, 2012, Brannan.
U.S. Appl. No. 13/711,086, Dec. 11, 2012, Brannan.
U.S. Appl. No. 13/711,164, filed Dec. 11, 2012, Brannan.
U.S. Appl. No. 13/734,638, filed Jan. 4, 2013, Bonn.
U.S. Appl. No. 13/740,706, filed Jan. 14, 2013, Rossetto.
U.S. Appl. No. 13/740,754, filed Jan. 14, 2013, Prakash.
Anonymous. (1987) Homer Mammalok™ Breast Lesion Needle/Wire Localizer, Namic® Angiographic Systems Division, Glens Falls, New York, (Hospital products price list), 4 pages.
C. F. Gottlieb et al., "Interstitial Microwave Hyperthermia Applicators having Submillimetre Diameters", Int, J. Hyperthermia, vol. 6, No. 3, pp. 707-714, 1990.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chung et al., "Clinical Experience of Sutureless Closed Hemorrhoidectomy with LigaSure™ " Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Goldberg et al., "Image-guided Radiofrequency Tumor Ablation: Challenges and Opportunities—Part I", (2001) J Vase. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Herman at al., "Laparoscopic Intestinal Resection With the LigaSure™ Vessel Sealing System: A Case Report" Innovations That Work, Feb. 2002.
Humphries Jr. et al., "Finite-Element Codes to Model Electrical Heating and Non-Llnear Thermal Transport in Biological Media", Proc. ASME HTD-355, 131 (1997).
Jarrett et al., "Use of the LigaSure™ Vessel Sealing System for Peri-Hilar Vessels in Laparoscopic Nephrectomy" Sales/Product Literature 2000.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, Vol., BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph Ortenberg, " LigaSure™ System Used in Laparoscopic 1st and 2nd Stage Orchiopexy" Innovations That Work, Nov. 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Ni Wei et al., "A Signal Processing Method for the Coriolis Mass Flowmeter Based on a Normalized . . . " Journal of Applied Sciences—Yingyong Kexue Xuebao, Shangha CN, vol. 23, No. 2:(Mar. 2005); pp. 160-184.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
R. Gennari et al., (Jun. 2000) "Use of Technetium-99m—Labeled Colloid Albumin for Preoperative and Intraoperative Localization of Non palpable Breast Lesions," American College of Surgeons. 190(6):692-699.
Rothenberg et al., "Use of the LigaSure™ Vessel Sealing System in Minimally Invasive Surgery in Children" Int'l Pediatric Endosurgery Group (1 PEG) 2000.
Solbiati et al. (1995) "Percutaneous US-guided RF Tissue Ablation of Liver Metastases: Long-term Follow-up", Radiology, pp. 195-203.
T. Seki et al., (1994) "Ultrasonically Guided Percutaneous Microwave Coagulation Therapy for Small Hepatocellular Carcinoma," Cancer 74(3):817•825.
Urologix, Inc.—Medical Professionals: Targis™ Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169(3):845-847.
W. Scott Helton, "LigaSure™ Vessel Sealing System: Revolutionary Hemostasis Product for General Surgery" Sales/Product Literature 1999.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.

(56) References Cited

OTHER PUBLICATIONS

European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US011/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Johnson et al., "Evaluation of a Bipolar Electrothermal Vessel Sealing Device in Hemorrhoidectomy" Sales/Product Literature, Jan. 2004.
Jarrett et al., "Use of the LigaSure.TM. Vessel Sealing System for Peri-Hilar Vessels in Laparoscopic Nephrectomy" Sales/Product Literature 2000.
Johnson, "Evaluation of the LigaSure.TM. Vessel Sealing System in Hemorrhoidectomy" American College of Surgeons (ACS) Clinic La Congress Poster (2000).
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Mar. 2000) I'D Wire: product description, 1 page.
MDTECH product literature (Dec. 1999) "FlexStrand": product description, 1 page.
Medtrex Brochure "The O.R. Pro 300" 1 page, Sep. 1998.
Michael Choti, "Abdominoperineal Resection with the LigaSure. TM. Vessel Sealing System and LigaSure.TM. Atlas 20 cm Open Instrument" Innovations That Work, Jun. 2003.
Muller et al., "Extended Left Hemicolectomy Using the LigaSure. TM. Vessels Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
S. Humphries Jr. et al., "Finite.cndot.Element Codes to Model Electrical Heating and Non.cndot.Llnear Thermal Transport in Biological Media", Proc. ASME HTD-355, 131 (1997).
Urologix, Inc.—Medical Professionals: Targis.TM. Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.

(56) References Cited

OTHER PUBLICATIONS

Vallfors et al., "Automatically Controlled Bipolar Electrocoagulation—'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
US. Appl. No. 08/483,742, filed Jun. 7, 1995, Stern et al.
U.S. Appl. No. 08/136,098, filed Oct. 14, 1993, Stern.
U.S. Appl. No. 09/195,118, filed Nov. 18, 1998.
U.S. Appl. No. 10/244,346, filed Sep. 16, 2002.
U.S. Appl. No. 11/053,987, filed Feb. 8, 2005.
U.S. Appl. No. 12/023,606, filed Jan. 31, 2008.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/351,633, filed Jan. 9, 2009.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/401,268, filed Mar. 10, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.

Ni Wei et al., "A Signal Processing Method for the Coriolis Mass Flowmeter Based on a Normalized . . . " Journal of Applied Sciences. cndot.Yigyong Kexue Xuebao, Shangha CN, vol. 23, No. 2:(Mar. 2005); pp. 160-184, Abstract only.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
Organ, L W., "Electrophysiologic Principles of Radiofrequency Lesion Making" Appl. Neurophysiol, vol. 39: pp. 69-76 (1976/1977).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.

(56) References Cited

OTHER PUBLICATIONS

Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
European Search Report for European Application No. 11010093.0 dated Mar. 20, 2012.
European Search Report for European Application No. 11010176.3 dated Mar. 19, 2012.
European Search Report for European Application No. 11010177.1 dated May 2, 2012.
European Search Report for European Application No. 11010175.5 dated Apr. 26, 2012.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C.F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.

Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM. " Diseases of the Colon & Rectum, vol. 46, No. 1, Jan. 2003.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Cosman et al., "Methods of Making Nervous System Lesions" in William RH, Rengachary SS (eds): Neurosurgery, New York: McGraw.cndot.Hill, vol. 111, (1984), pp. 2490-2499.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline Product Literature, "Light Key: Visualize a Virtual Keyboard. One With No Moving Parts", 4 pages, Nov. 1, 2003.
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radio!, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Heniford et al., "Initial Results with an Electrothermal Bipolar Vessel Sealer" Surgical Endoscopy (2001) 15:799-801.
Herman at al., "Laparoscopic Intestinal Resection With the LigaSure.TM. Vessel Sealing System: A Case Report" Innovations That Work, Feb. 2002.
Anderson at al., "A Numerical Study of Rapid Heating for High Temperature Radio Frequency Hyperthermia" International Journal of Bio-Medical Computing, 35 (1994), pp. 297-307.
Anobymous. (1987) Homer Mammalok™ Breast Lesion Needle/Wire Localizer, Namic® Angiographic Systems Division, Glens Falls, New York, (Hospital products price list), 4 pages.
C. F. Gottlieb et al., "Interstitial Microwave Hyperthermia Applicators having Submillimetre Diameters", Int. J. Hyperthermia, vol. 6, No. 3, pp. 707-714, 1990.
Chung et al,, "Clinical Experience of Sutureless Closed Hemorrhoidectomy with LigaSure™" Diseases of the Colon & Rectum, vol. 46, No. 1, Jan. 2003.
Cosinan et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Cosman et al., "Methods of Making Nervous System Lesions" in William RH, Rengachary SS (eds): Neurosurgery, New York: McGraw•Hill, vol. 111, (1984), pp. 2490-2499.

(56) References Cited

OTHER PUBLICATIONS

Goldberg et al., "Image-guided Radiofrequency Tumor Ablation: Challenges and Opportunities—Part I", (2001) J Vasc. Interv. Radiol, vol. 12, pp. 1021-1032.
Heniford et al,, "Initial Results with an Electrothermal Bipolar Vessel Sealer" Surgical Endoscopy (2001) 15:799-801.
Ian D. McRury et al,, The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Joseph Ortenberg, "LigaSure™ System Used in Laparoscopic 1st and 2nd Stage Orchiopexy" Innovations That Work, Nov. 2002.
Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.
Paul G. Horgan, "A Novel Technique for Parenchymal Division During Hepatectomy" The American Journal of Surgery, vol. 181, No.3, Apr. 2001, pp, 236-237.
Rothenberg et al., "Use of the LigaSure™ Vessel Sealing System in Minimally Invasive Surgery in Children" Int'l Pediatric Endosurgery Group (I PEG) 2000.
Sigel et al,, "The Mechanism of Blood Vessel Closure by High Frequency Electrocoagulation" Surgery Gynecology & Obstetrics, Oct. 1965 pp. 823-831.
S. Humphries Jr. et al., "Finite•Element Codes to Model Electrical Heating and Non•Llnear Thermal Transport in Biological Media", Proc. ASME HTD-355, 131 (1997).
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Valleylab Brochure, "Valleylab Electroshield Monitoring System" 2 pages; Nov. 1995.
Copy of European Search Report EP 03721482 dated Feb. 6, 2006.
Copy of European Search Report EP 04009964 dated Jul. 28, 2004.
Copy of European Search Report EP 04013772 dated Apr. 11, 2005.
Copy of European Search Report EP 04015980 dated Nov. 3, 2004.
Copy of European Search Report EP 04015981.6 dated Oct. 25, 2004.
Copy of European Search Report EP 04027314 dated Mar. 31, 2005.
Copy of European Search Report EP 04027479 dated Mar. 17, 2005.
Copy of European Search Report EP 04027705 dated Feb. 10, 2005.
Copy of European Search Report EP 04710258 dated Oct. 15, 2004.
Copy of European Search Report EP 04752343.6 dated Jul. 31, 2007.
Copy of European Search Report EP 05002027.0 dated May 12, 2005.
Copy of European Search Report EP 05002769.7 dated Jun. 19, 2006.
Copy of European Search Report EP 05013463.4 dated Oct. 7, 2005.
Copy of European Search Report EP 05013895 dated Oct. 21, 2005.
Copy of European Search Report EP 05014156.3 dated Jan. 4, 2006.
Copy of European Search Report EP 05016399 dated Jan. 13, 2006.
Copy of European Search Report EP 05017281 dated Nov. 24, 2065.
Copy of European Search Report EP 05019130.3 dated Oct. 27, 2005.
Copy of European Search Report EP 05019882 dated Feb. 16, 2006.
Copy of European Search Report EP 05020665.5 dated Feb. 27, 2006.
Copy of European Search Report EP 05020666.3 dated Feb. 27, 2006.
Copy of European Search Report EP 05021025.1 dated Mar. 13, 2006.
Copy of European Search Report EP 05021197.8 dated Feb. 20, 2006.
Copy of European Search Report EP 05021777 dated Feb. 23, 2006.
Copy of European Search Report EP 05021779.3 dated Feb. 2, 2006.
Copy of European Search Report EP 05021780.1 dated Feb. 23, 2006.
Copy of European Search Report EP 05021935 dated Jan. 27, 2006.
Copy of European Search Report EP 05021936.9 dated Feb. 6, 2006.
Copy of European Search Report EP 05021937.7 dated Jan. 23, 2006.
Copy of European Search Report EP 05021939 dated Jan. 27, 2006.
Copy of European Search Report EP 05021944.3 dated Jan. 25, 2006.
Copy of European Search Report EP 05022350.2 dated Jan. 30, 2006.
Copy of European Search Report EP 05023017.6 dated Feb. 24, 2006.
Copy of European Search Report EP 05025423.4 dated Jan. 19, 2007.
Copy of European Search Report EP 05025424 dated Jan. 30, 2007.
Copy of European Search Report EP 06000708.5 dated May 15, 2006.
Copy of European Search Report EP 06002279.5 dated Mar. 30, 2006.
Copy of European Search Report EP 06005185.1 dated May 10, 2006.
Co), of European Search Report EP 06005540 dated Sep. 24, 2007.
Copy of European Search Report EP 06006717.0 dated Aug. 11, 2006.
Copy of European Search Report EP 06006961 dated Oct. 22, 2007.
Copy of European Search Report EP 06006963 dated Jul. 25, 2006.
Copy of European Search Report EP 06008779.8 dated Jul. 13, 2006.
Copy of European Search Report EP 06009435 dated Jul. 13, 2006.
Copy of European Search Report EP 06010499.9 dated Jan. 29, 2008.
Copy of European Search Report EP 06014461.5 dated Oct. 31, 2006.
Copy of European Search Report EP 06018206.0 dated Oct. 20, 2006.
Copy of European Search Report EP 06019768 dated Jan. 17, 2007.
Copy of European Search Report EP 06020574.7 dated Oct. 2, 2007.
Copy of European Search Report EP 06020583.8 dated Feb. 7, 2007.
Copy of European Search Report EP 06020584.6 dated Feb. 1, 2007.
Copy of European Search Report EP 06020756.0 dated Feb. 16, 2007.
Copy of European Search Report EP 06022028,2 dated Feb. 13, 2007.
Copy of European Search Report EP 06023756.7 dated Feb. 21, 2008.
Copy of European Search Report EP 06024122.1 dated Apr. 16, 2007.
Copy of European Search Report EP 06024123.9 dated Mar. 6, 2007.
Copy of European Search Report EP 06025700.3 dated Apr. 12, 2007.
Copy of European Search Report EP 07000885.9 dated May 15, 2007.
Copy of European Search Report EP 07001480.8 dated Apr. 19, 2007.
Copy of European Search Report EP 07001481,6 dated May 2, 2007.
Copy of European Search Report EP 07001485.7 dated May 23, 2007.
Copy of European Search Report EP 07001488.1 dated Jun. 5, 2007.
Copy of European Search Report EP 07001489.9 dated Dec. 20, 2007.
Copy of European Search Report EP 07001491 dated Jun. 6, 2007.
Copy of European Search Report EP 07001527.6 dated May 18, 2007.
Copy of European Search Report EP 07007783.9 dated Aug. 14, 2007.
Copy of European Search Report EP 07008207.8 dated Sep. 13, 2007.
Copy of European Search Report EP 07009026.1 dated Oct. 8, 2007.
Copy of European Search Report EP 07009028 dated Jul. 16, 2007.
Copy of European Search Report EP 07009029.5 dated Jul. 20, 2007.
Copy of European Search Report EP 07009321.6 dated Aug. 28, 2007.
Copy of European Search Report EP 07009322.4 dated Jan. 14, 2008.
Copy of European Search Report EP 07010672.9 dated Oct. 16, 2007.
Copy of European Search Report EP 07010673.7 dated Oct. 5, 2007.
Copy of European Search Report EP 07013779.9 dated Oct. 26, 2007.
Copy of European Search Report EP 07015191.5 dated Jan. 23, 2007.
Copy of European Search Report EP 07015601.3 dated Jan. 4, 2007.
Copy of European Search Report EP 07015602.1 dated Dec. 20, 2007.

(56) References Cited

OTHER PUBLICATIONS

Copy of European Search Report EP 07018375.1 dated Jan. 8, 2008.
Copy of European Search Report EP 07018821 dated Jan. 14, 2008.
Copy of European Search Report EP 01019173.9 dated Feb. 12, 2008.
Copy of European Search Report EP 07019174.7 dated Jan. 29, 2008.
Copy of European Search Report EP 07019178.8 dated Feb. 12, 2008.
Copy of European Search Report EP 07020283,3 dated Feb. 5, 2008.
Copy of European Search Report EP 07253835.8 dated Dec. 20, 2007.
Copy of European Search Report EP 08001019 dated Sep. 23, 2008.
Copy of European Search Report EP 08004975 dated Jul. 24, 2008.
Copy of European Search Report EP 08006731.7 dated Jul. 29, 2008.
Copy of European Search Report EP 08006733 dated Jul. 7, 2008.
Copy of European Search Report EP 08006734.1 dated Aug. 18, 2008.
Copy of European Search Report EP 08006735.8 dated Jan. 8, 2009.
Copy of European Search Report EP 08015842 dated Dec. 5, 2008.
Copy of European Search Report EP 98300964.8 dated Dec. 13, 2000.
Copy of European Search Report EP 98944778 dated Nov. 7, 2000.
Copy of European Search Report EP 98958575.7 dated Oct. 29, 2002.
Copy of International Search Report PCT/US01/11218 dated Aug. 14, 2001.
Copy of International Search Report PCT/US01/11224 dated Nov. 13, 2001.
Copy of International Search Report PCT/US01/11340 dated Aug. 16, 2001.
Copy of International Search Report PCT/US01/11420 dated Oct. 16, 2001.
Copy of International Search Report PCT/US02/01890 dated Jul. 25, 2002.
Copy of International Search Report PCT/US02/11100 dated Jul. 16; 2002.
Copy of International Search Report PCT/US03/09483 dated Aug. 13, 2003.
Copy of International Search Report PCT/US03/22900 dated Dec. 2, 2003.
Copy of International Search Report PCT/US03/37110 dated Jul. 25, 2005.
Copy of International Search Report PCT/US03/37111 dated Jul. 28, 2004.
Copy of International Search Report PCT/US03/37310 dated Aug. 13, 2004.
Copy of International Search Report PCT/US04/04685 dated Aug. 27, 2004.
Copy of International Search Report PCT/US04/13273 dated Dec. 15, 2004.
Copy of International Search Report PCT/US04/15311 dated Jan. 12, 2004.
Copy of International Search Report PCT/US98/18640 dated Jan. 29, 1998.

* cited by examiner

OPTICAL DETECTION OF INTERRUPTED FLUID FLOW TO ABLATION PROBE

CROSS-REFERENCE TO RELATED APPLICATIONS

The present application is a divisional application, which claims priority to, and the benefit of, U.S. patent application Ser. No. 12/566,299, filed on Sep. 24, 2009, the disclosure of which is herein incorporated by reference in its entirety.

BACKGROUND

1. Technical Field

The present disclosure relates to detection devices for use in electrosurgical devices and, more particularly, to systems and methods for optical detection of interrupted fluid flow to an ablation probe.

2. Discussion of Related Art

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic radiation to heat, ablate and/or coagulate tissue. Microwave energy is sometimes utilized to perform these methods. Other procedures utilizing electromagnetic radiation to heat tissue also include coagulation, cutting and/or ablation of tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator that functions as an energy source, and a microwave surgical instrument (e.g., microwave ablation probe) having an antenna assembly for directing the energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

There are several types of microwave probes in use, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors, which are linearly aligned and positioned end-to-end relative to one another with an electrical insulator placed therebetween. Helical antenna assemblies include a helically-shaped conductor that can be formed in various configurations. The main modes of operation of a helical antenna assembly are normal mode (broadside), in which the field radiated by the helix is maximum in a perpendicular plane to the helix axis, and axial mode (end fire), in which maximum radiation is along the helix axis.

A microwave transmission line typically includes a thin inner conductor that extends along the longitudinal axis of the transmission line and is surrounded by a dielectric material and is further surrounded by an outer conductor around the dielectric material such that the outer conductor also extends along the transmission line axis. In one variation of an antenna, a waveguiding structure, such as a length of transmission line or coaxial cable, is provided with a plurality of openings through which energy "leaks" or radiates away from the guiding structure. This type of construction is typically referred to as a "leaky coaxial" or "leaky wave" antenna.

Cooling the ablation probe may enhance the overall heating pattern of the antenna, prevent damage to the antenna and prevent harm to the clinician or patient. Because of the small temperature difference between the temperature required for denaturing malignant cells and the temperature normally injurious to healthy cells, a known heating pattern and precise temperature control is needed to lead to more predictable temperature distribution to eradicate the tumor cells while minimizing the damage to surrounding normal tissue.

Fluid cooled or dielectrically buffered microwave devices may be used in ablation procedures. During operation of a microwave ablation device, if proper cooling is not maintained, e.g., flow of coolant or buffering fluid is interrupted, the microwave ablation device may exhibit rapid failures due to the heat generated from the increased reflected power. A coolant fluid having entrained gas bubbles may be circulated from a cooling system into a microwave ablation device. When a bubble filled with even a small volume of air or multiple air bubbles in close proximity to each other are introduced into an ablation probe, e.g., when the ablation probe is operating at a high power level, the ablation probe may be susceptible to rapid failure due to overheating conditions. The time to failure is dependant on the power delivered to the antenna and degree to which coolant flow is reduced and/or the duration of the interruption.

SUMMARY

The present disclosure relates to an electrosurgical system including an electrosurgical device adapted to direct energy to tissue and a fluid path leading to the electrosurgical device. The system also includes an optical sensor unit operably associated with the fluid path. The optical sensor unit includes a light-emitting element to generate light output and a light-receiving element to collect light outputted from the light-emitting element. The light-emitting element and the light-receiving element are disposed such that light output from the light-emitting element passes through the fluid path to the light-receiving element. The optical sensor unit is capable of detecting an air bubble in the fluid path passing through the optical sensor unit using a sensed characteristic of light collected at the light-receiving element.

The present disclosure also relates to a method of detecting an air bubble in a fluid flow including the step of providing an optical sensor unit including a light-emitting element and a light-receiving element, the optical sensor unit operably associated with a fluid path. The method also includes the steps of determining a first reference value based on air flow in the fluid path passing through the optical sensor, determining a second reference value based on fluid flow in the fluid path passing through the optical sensor unit, using the optical sensor unit to monitor the fluid flow in the fluid path to detect an air bubble in the fluid flow using at least one of the first reference value or the second reference value, and when an air bubble in the fluid flow is detected by the optical sensor unit, outputting an electrical signal from the optical sensor unit.

The present disclosure also relates to a method of detecting an air bubble in a fluid flow including the step of providing a fluid source for supplying a fluid and providing an optical sensor unit including a light-emitting element and a light-receiving element, the optical sensor unit operably associated with a first fluid path, the first fluid path leading from the fluid source to an electrosurgical device. The method also includes the steps of: performing a first calibration step by directing light from the light-emitting element through air flow in the first fluid path passing through the optical sensor unit and sensing a characteristic of light collected at the light-receiving element to determine a first reference value; performing a second calibration step by directing light from the light-emitting element through fluid flow in the first fluid path passing through the optical sensor unit and sensing a characteristic of light collected at the light-receiving element to determine a second reference value; operating the optical sensor unit to direct light from the light-emitting element through the first fluid path passing through the optical sensor unit and to sense a characteristic of light collected at the light-receiving element to determine a third reference value; and controlling an electrosurgical generator based on a comparison result of a comparison of the third reference value to the first and second reference values.

BRIEF DESCRIPTION OF THE DRAWINGS

Objects and features of the presently disclosed systems and methods for optical detection of interrupted fluid flow to an electrosurgical device will become apparent to those of ordinary skill in the art when descriptions of various embodiments thereof are read with reference to the accompanying drawings, of which.

DETAILED DESCRIPTION

Hereinafter, embodiments of the presently disclosed systems and methods for optical detection of interrupted fluid flow to an electrosurgical device are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus that is closer to the user and the term "distal" refers to that portion of the apparatus that is further from the user.

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As it is used in this description, "ablation procedure" generally refers to any ablation procedure, such as microwave ablation, radio frequency (RF) ablation or microwave ablation-assisted resection.

Light may be regarded as an electromagnetic wave that travels in straight lines (gravity and electromagnetic influences excepted) until it is either reflected or refracted. Refraction of light occurs when a light wave travels from a medium with a given refractive index to a medium with another refractive index. As it is used in this description, "refraction" generally refers to the change in direction of a wave due to a change in its speed, as occurs when a wave passes from one medium to another. As it is used in this description, "refractive index" generally refers to a measure of how much the speed of light is reduced inside a medium, compared to the speed of light in vacuum or air.

As it is used in this description, "light source" generally refers to all illumination sources including photo-luminescent sources, fluorescent sources, phosphorescence sources, lasers, electro-luminescent sources, such as electro-luminescent lamps, and light-emitting diodes. As it is used in this description, "light-emitting diode" generally refers to any system that is capable of receiving an electrical signal and producing a color of light in response to the signal. Thus, "light-emitting diode", as used herein, includes light-emitting diodes (LEDs) of all types, including white LEDs, infrared LEDs, ultraviolet LEDs, visible color LEDs, light-emitting polymers, semiconductor dies that produce light in response to current, organic LEDs, electro-luminescent strips, silicon based structures that emit light, and other such systems. As it is used in this description, "color" generally refers to any frequency of electromagnetic radiation, or combination of different frequencies, within the visible light spectrum, the infrared and ultraviolet areas of the spectrum, and in other areas of the electromagnetic spectrum where illumination sources may generate radiation.

As it is used in this description, "optical detector" generally refers to a device that converts an optical signal into an electrical signal. As it is used in this description, "transmission line" generally refers to any transmission medium that can be used for the propagation of signals from one point to another. As it is used in this description, "fluid" generally refers to a liquid, a gas or both.

Various embodiments of the present disclosure provide electrosurgical devices for treating tissue and systems and methods for optical detection of interrupted fluid flow to the electrosurgical devices, such as ablation probes. Embodiments may be implemented using electromagnetic radiation at microwave frequencies or at other frequencies. An electrosurgical system including an energy applicator in fluid communication with a coolant supply system, according to various embodiments, is designed and configured to operate between about 500 MHz and about 10 GHz. The coolant supply system, as described herein, may be used in conjunction with various types of devices, such as microwave antennas having either a straight or looped radiating antenna portion, etc.

Various embodiments of the presently disclosed electrosurgical systems including an energy applicator in fluid communication with a coolant supply system are suitable for microwave ablation and for use to pre-coagulate tissue for microwave ablation assisted surgical resection. Although various methods described hereinbelow are targeted toward microwave ablation and the complete destruction of target tissue, it is to be understood that methods for directing electromagnetic radiation may be used with other therapies in which the target tissue is partially destroyed or damaged, such as, for example, to prevent the conduction of electrical impulses within heart tissue. In addition, although the following description describes the use of a dipole microwave antenna, the teachings of the present disclosure may also apply to a monopole, helical, or other suitable type of microwave antenna.

Figure 1:
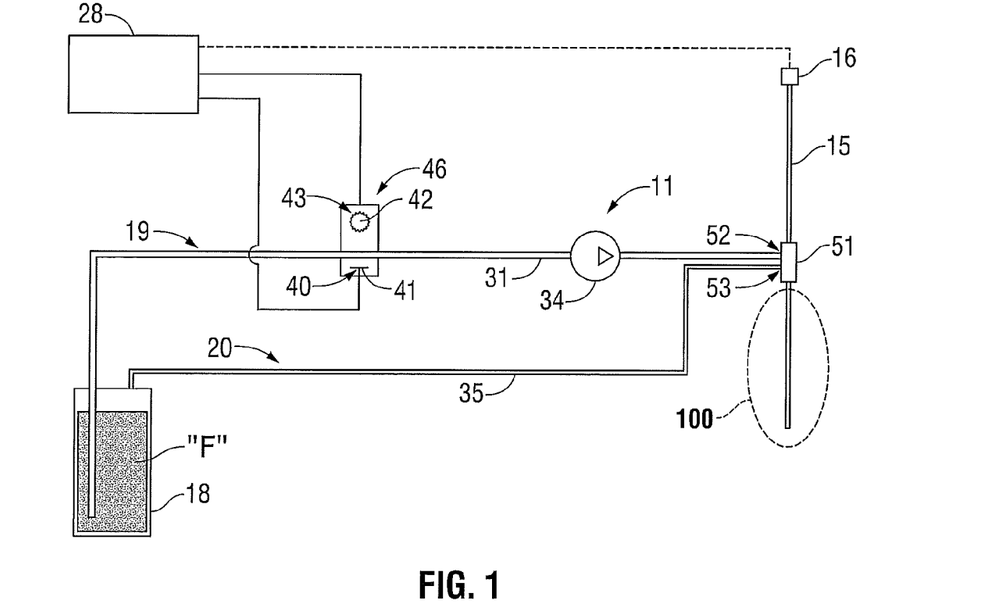
FIG. 1 is a schematic diagram of an electrosurgical system including a coolant supply system according to an embodiment of the present disclosure.

FIG. 1 shows an electrosurgical system 10 according to an embodiment of the present disclosure that includes an energy applicator or probe 100. An embodiment of an energy applicator, such as the probe 100 of FIG. 1, in accordance with the present disclosure, is shown in more detail in FIG. 2. It will be understood, however, that other probe embodiments may also be used.

Probe 100, which is described in more detail later in this disclosure, generally includes an antenna assembly 12 having a radiating portion connected by a feedline 110 (or shaft) via a transmission line 15 to a connector 16, which may further operably connect the probe 100 to a power generating source 28, e.g., a microwave or radio frequency (RF) electrosurgical generator. Feedline 110 may be coupled to a coolant port 51 to facilitate the flow of coolant or buffering fluid into, and out of, the probe 100.

Electrosurgical system 10 in accordance with an embodiment of the present disclosure includes a power generating source 28, a coolant supply system 11 adapted to provide coolant fluid "F" to the probe 100, and a sensor unit 46 capable of detecting a gas bubble in the coolant supply system 11. In some embodiments, the sensor unit 46 is electrically coupled to the power generating source 28, and may be configured to generate an alarm signal to the power generating source 28 and, in response thereto, control logic, which may be associated with the power generating source 28, may reduce the power output, e.g., for a predetermined time interval or until a manual reset switch is actuated.

In some embodiments, the coolant supply system 11 includes a coolant source 18, and may include a substantially closed loop having a first coolant path 19 leading to the probe 100 and a second coolant path 20 leading from the probe 100. The size and shape of the first coolant path 19 and the second coolant path 20 may be varied from the configuration depicted in FIG. 1. Sensor unit 46 may be configured to detect an air bubble in close proximity to the coolant source 18.

Coolant port 51 may be in fluid communication with the coolant source 18 via the first coolant path 19 and/or the second coolant path 20. In some embodiments, the coolant supply system 11 includes a first coolant path 19 and a second coolant path 20, wherein the first coolant path 19 includes a coolant supply line 31 leading from the coolant source 18 to a coolant inlet port 52 that is defined in the coolant port 51, and the second coolant path 20 includes a coolant return line 35 leading from a coolant outlet port 53 that is defined in the coolant port 51 to the coolant source 18.

Coolant source 18 may be any suitable housing containing a reservoir of coolant fluid "F". Coolant fluid "F" may be any suitable fluid that can be used for cooling or buffering the probe 100, e.g., deionized water, or other suitable cooling medium. Coolant fluid "F" may have dielectric properties and may provide dielectric impedance buffering for the antenna assembly 12. Coolant fluid "F" may be a conductive fluid, such as a saline solution, which may be delivered to the target tissue, e.g., to decrease impedance and allow increased power to be delivered to the target tissue. A coolant fluid "F" composition may vary depending upon desired cooling rates and the desired tissue impedance matching properties. Various fluids may be used, e.g., liquids including, but not limited to, water, saline, perfluorocarbon, such as the commercially available Fluorinert® perfluorocarbon liquid offered by Minnesota Mining and Manufacturing Company (3M), liquid chlorodifluoromethane, etc. In other variations, gases (such as nitrous oxide, nitrogen, carbon dioxide, etc.) may also be utilized as the cooling fluid. In yet another variation, a combination of liquids and/or gases, including, for example, those mentioned above, may be utilized as the coolant fluid "F".

As shown in FIG. 1, a fluid movement device 34 may be provided in the first coolant path 19 to move the coolant fluid "F" through the first coolant path 19. Fluid movement device 34 may include valves, pumps, power units, actuators, fittings, manifolds, etc. The position of the fluid movement device 34 may be varied from the configuration depicted in FIG. 1. Fluid movement device 34 may additionally, or alternatively, be provided in the second coolant path 20. Although the coolant supply system 11 shown in FIG. 1 includes a single, fluid movement device 34 positioned in the first coolant path 19, various combinations of different numbers of fluid movement devices, variedly sized and variedly spaced apart from each other, may be provided in the first coolant path 19 and/or the second coolant path 20.

Sensor unit 46 may be disposed at any suitable position to allow for the detection of a gas bubble in the coolant supply system 11. In some embodiments, the sensor unit 46 is disposed such that a gas bubble in the coolant supply system 11 can be detected before the bubble can be introduced into the probe 100. Sensor unit 46 may be disposed in the first coolant path 19, and may be disposed in close proximity to the coolant source 18. In some embodiments, the sensor unit 46 is electrically coupled to the power generating source 28, and the detection of a bubble may trigger an alarm signal to the power generating source 28. Electrical characteristics of the power generating source 28 may be controlled in response to the alarm signal. In some embodiments, the electrosurgical system 10 reduces the power and/or voltage output of the power generating source 28, thereby reducing energy applicator power output to a low level, in response to the alarm signal. In some embodiments, the sensor unit 46 includes an optical detector, and may be used to monitor the coolant fluid "F" flow in the coolant supply line 31 to detect the presence of air or other gas within the coolant fluid "F" flow.

Audible indicatory means may be incorporated or associated with the electrosurgical system 10 to notify the operator of the bubble condition. In such case, the operator may take steps, e.g., perform visual inspection of the coolant fluid "F" in the coolant source 18 and/or visual inspection of the first coolant path 19, or portions thereof, to verify that the coolant supply system 11 is functioning properly. A "reset" button (not shown) may be provided to allow the power generating source 28 to return to normal mode.

In the illustrated embodiment, sensor unit 46 generally includes a light source or light-emitting element 43 (also referred to herein as optical transmitter 43) and a light receiving element 40 (also referred to herein as optical receiver 40). Optical transmitter 43 may include any suitable device configured to transmit optical signals, e.g., a light-emitting diode (LED) 42. Optical receiver 40 may include any suitable device configured to receive optical signals, e.g., a photo-diode 41. In some embodiments, an LED 42 and a photo-diode 41 are arranged on opposite sides of a coolant line, e.g., the coolant supply line 31. LED 42 may be configured to transmit either a continuous or pulsed optical signal through the coolant supply line 31. Photo-diode 41 may be positioned to receive the transmitted optical signal on the opposite side of the coolant supply line 31 from the LED 42. A fixture housing an LED 42 and photo-diode 41 pair may be provided to allow the sensor unit 46 (also referred to herein as optical detector 46) to be clipped or otherwise fastened to a portion of the coolant supply line 31, e.g., to provide reliable orientation and shield the optical detector 46 from ambient light interference.

In accordance with embodiments of the present disclosure, an air or other gas bubble may be detected by the optical detector 46 by either signal intensity or signal position at the optical receiver 40. Air and liquids have different degrees of attenuation per unit length and different refractive index values (e.g., water has a higher refractive index than air). Air has a refractive index of about 1.0003, and water has a refractive index of about 1.33. When an air bubble passes through the coolant supply line 31, the optical detector 46, according to embodiments of the present disclosure, detects the change in intensity of light collected at the photo-diode 41, compared to the intensity of light collected at the photo-diode 41 when fluid "F" passes through the coolant supply line 31. In sensor unit 46 embodiments using signal intensity to detect an air bubble, the change in intensity of light collected at the photo-diode 41 is interpreted as indicator of the presence of an air bubble.

In some embodiments, an LED 42 and a photo-diode 41 are configured to communicate when fluid "F" is present in the coolant supply line 31. When an air bubble passes through the coolant supply line 31, the varied refraction angle deflects light away from its intended photo-diode 41 and very little light impinges upon the photo-diode 41. In sensor unit 46 embodiments using signal position to detect an air bubble, the absence of light impinging upon the photo-diode 41 is interpreted as indicator of the presence of an air bubble.

A logic circuit (not shown) in the sensor unit 46 may relay information through digital or analog communication to the power generating source 28 indicating whether the optical detector 46 is in the no-bubble state or bubble state. The optical detector 46 may be a separate device that plugs into digital or analog inputs on the power generating source 28, programmed according to the communication protocol of the optical detector 46.

In some embodiments, the power generating source 28 is configured to provide microwave energy at an operational frequency from about 500 MHz to about 2500 MHz. In other embodiments, the power generating source 28 is configured to provide microwave energy at an operational frequency from about 500 MHz to about 10 GHz. Power generating source 28 may be configured to provide various frequencies of electromagnetic energy. Transmission line 15 may additionally, or alternatively, provide a conduit (not shown) configured to provide coolant fluid "F" from the coolant source 18 to the probe 100.

Figure 2:
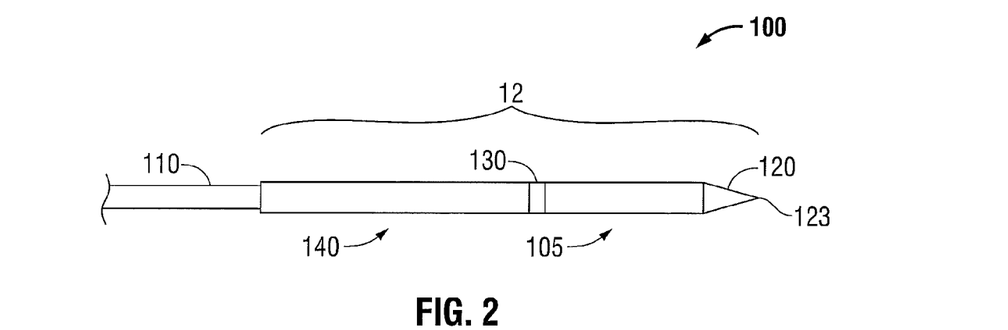
FIG. 2 is an enlarged view of the indicated area of detail of FIG. 1 according to an embodiment of the present disclosure.

Feedline 110 may electrically connect the antenna assembly 12 via the transmission line 15 to the power generating source 28, and may include a coaxial cable, which may be semi-rigid or flexible. Feedline 110 may have a variable length from a proximal end of the antenna assembly 12 to a distal end of transmission line 15 ranging from a length of about one inch to about twelve inches. Feedline 110 may be constructed of a variety of electrically conductive materials, e.g., copper, gold, or other conductive metals with similar conductivity values. Feedline 110 may be made of stainless steel, which generally offers the strength required to puncture tissue and/or skin. Conductive materials used to form the feedline 110 may be plated with other materials, e.g., other conductive materials, to improve their properties, e.g., to improve conductivity or decrease energy loss, etc.

In some embodiments, the feedline 110 includes stainless steel, and to improve its conductivity, the stainless steel may be coated with a layer of a conductive material such as copper or gold. Feedline 110 may include an inner conductor, a dielectric material coaxially surrounding the inner conductor, and an outer conductor coaxially surrounding the dielectric material. Antenna assembly 12 may be formed from a portion of the inner conductor that extends distal of the feedline 110 into the antenna assembly 12. In one embodiment, the feedline 110 may be formed from a coaxial, semi-rigid or flexible cable having a wire with a 0.047" outer diameter rated for 50 Ohms. Feedline 110 may be cooled by fluid e.g., saline or water, to improve power handling, and may include a stainless steel catheter.

Located at the distal end of the antenna assembly 12 is an end cap or tapered portion 120, which may terminate in a sharp tip 123 to allow for insertion into tissue with minimal resistance. One example of a straight probe with a sharp tip that may be suitable for use as the energy applicator 100 is commercially available under the trademark EVIDENT™ offered by Covidien. The end cap or tapered portion 120 may include other shapes, such as, for example, a tip 123 that is rounded, flat, square, hexagonal, or cylindroconical.

In some variations, the antenna assembly 12 includes a distal radiating portion 105 and a proximal radiating portion 140. In some embodiments, a junction 130 couples the proximal radiating portion 140 and the distal radiating portion 105. In some embodiments, the distal and proximal radiating portions 105, 140 align at the junction 130, which is generally made of a dielectric material, e.g., adhesives, and are also supported by the inner conductor that extends at least partially through the distal radiating portion 105. Junction 130, or portions thereof, may be disposed between the proximal and distal radiating portions, 140 and 105. Junction 130 may be formed from any suitable elastomeric or ceramic dielectric material by any suitable process. In some embodiments, the junction 130 is formed by overmolding and includes a thermoplastic elastomer, such as, for example, polyether block amide (e.g., PEBAX®, manufactured by The Arkema Group of Colombes, France), polyetherimide (e.g., ULTEM® and/or EXTEM®, manufactured by SABIC Innovative Plastics of Saudi Arabia) and/or polyimide-based polymer (e.g., VESPEL®, manufactured by E. I. du Pont de Nemours and Company of Wilmington, Del., United States). Junction 130 may be formed using any suitable overmolding compound by any suitable process, and may include use of a ceramic substrate.

Figure 3:
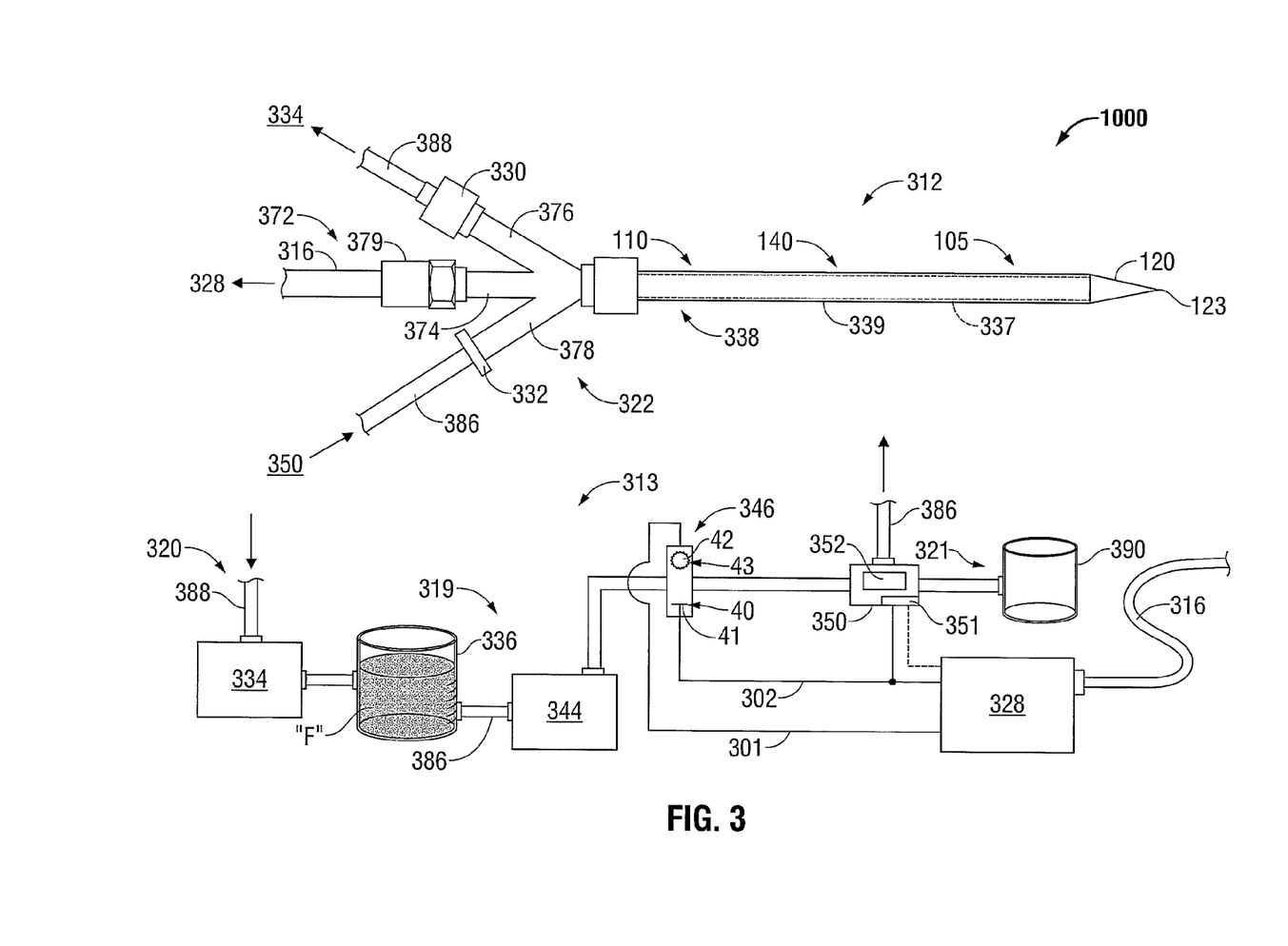
FIG. 3 is a schematic diagram of an electrosurgical system including a coolant supply system according to another embodiment of the present disclosure.

In some embodiments, the antenna assembly 12 may be provided with a coolant chamber (e.g., 337 shown in FIG. 3). Additionally, the junction 130 may include coolant inflow and outflow ports (not shown) to facilitate the flow of coolant into, and out of, the coolant chamber. Examples of coolant chamber and coolant inflow and outflow port embodiments are disclosed in commonly assigned U.S. patent application Ser. No. 12/401,268 filed on Mar. 10, 2009, entitled "COOLED DIELECTRICALLY BUFFERED MICROWAVE DIPOLE ANTENNA", and U.S. Pat. No. 7,311,703 entitled "DEVICES AND METHODS FOR COOLING MICROWAVE ANTENNAS".

In some embodiments, the antenna assembly 12 may be provided with an outer jacket (e.g., 339 shown in FIG. 3)

disposed about the distal radiating portion 105, the junction 130 and/or the proximal radiating portion 140. The outer jacket may be formed of any suitable material, such as, for example, polymeric or ceramic materials. The outer jacket may be applied by any suitable method, such as, for example, heat shrinking, overmolding, coating, spraying dipping, powder coating, baking and/or film deposition. The outer jacket may be a water cooled catheter formed of a material having low electrical conductivity.

During microwave ablation, e.g., using the electrosurgical system 10, the probe 100 is inserted into or placed adjacent to tissue and microwave energy is supplied thereto. Ultrasound or computed tomography (CT) guidance may be used to accurately guide the probe 100 into the area of tissue to be treated. Probe 100 may be placed percutaneously or atop tissue, e.g., using conventional surgical techniques by surgical staff. A clinician may pre-determine the length of time that microwave energy is to be applied. Application duration may depend on many factors such as tumor size and location and whether the tumor was a secondary or primary cancer. The duration of microwave energy application using the probe 100 may depend on the progress of the heat distribution within the tissue area that is to be destroyed and/or the surrounding tissue. Single or multiple probes 100 may provide ablations in short procedure times, e.g., a few minutes, to destroy cancerous cells in the target tissue region.

A plurality of probes 100 may be placed in variously arranged configurations to substantially simultaneously ablate a target tissue region, making faster procedures possible. Multiple probes 100 can be used to synergistically create a large ablation or to ablate separate sites simultaneously. Tissue ablation size and geometry is influenced by a variety of factors, such as the energy applicator design, number of energy applicators used simultaneously, time and wattage.

In operation, microwave energy having a wavelength, lamda ($\lambda$), is transmitted through the antenna assembly 12, e.g., along the proximal and distal radiating portions 140, 105, and radiated into the surrounding medium, e.g., tissue. The length of the antenna for efficient radiation may be dependent on the effective wavelength, $\lambda_{eff}$, which is dependent upon the dielectric properties of the medium being radiated into. Antenna assembly 12 through which microwave energy is transmitted at a wavelength, $\lambda$, may have differing effective wavelengths, $\lambda_{eff}$, depending upon the surrounding medium, e.g., liver tissue as opposed to breast tissue.

FIG. 3 shows an electrosurgical system 1000 according to an embodiment of the present disclosure that includes an antenna assembly 312 substantially disposed within a sheath 338. Antenna assembly 312 is similar to the antenna assembly 12 shown in FIG. 2 and further description thereof is omitted in the interests of brevity. In some embodiments, a feedline 110 couples the antenna assembly 312 to a connection hub 322. Connection hub 322, which is described in more detail later in this disclosure, generally includes a cable connector 379 and fluid ports 330 and 332.

Sheath 338 generally includes a tubular member 339 defining a lumen into which the antenna assembly 312, or portion thereof, may be positioned. In some embodiments, the sheath 338 is disposed over and encloses the feedline 110, the proximal radiating portion 140 and the distal radiating portion 105, and may at least partially enclose the tip 123. In accordance with the embodiment shown in FIG. 3, a coolant chamber 337 is defined between the tubular member 339 and the outer surfaces of the feedline 110, the proximal radiating portion 140 and the distal radiating portion 105. Coolant chamber 337 is adapted to circulate coolant fluid "F" therethrough, and may include baffles, multiple lumens, flow restricting devices, or other structures that may redirect, concentrate, or disperse flow depending on their shape. Examples of coolant chamber embodiments are disclosed in commonly assigned U.S. patent application Ser. No. 12/350,292 filed on Jan. 8, 2009, entitled "CHOKED DIELECTRIC LOADED TIP DIPOLE MICROWAVE ANTENNA". The size and shape of the sheath 338 and the coolant chamber 337 extending therethrough may be varied from the configuration depicted in FIG. 3.

Electrosurgical system 1000 in accordance with an embodiment of the present disclosure includes a power generating source 328, a coolant supply system 313 adapted to provide coolant fluid "F" via a connection hub 322 to the antenna assembly 312, and a sensor unit 346 capable of detecting a gas bubble in the coolant supply system 313 and electrically coupled via transmission lines 301 and 302 to the power generating source 328. Electrosurgical system 1000 may further include a flow-diverter apparatus 350 operably associated with the sensor unit 346 and disposed in fluid communication between the sensor unit 346 and the connection hub 322. In some embodiments, when the sensor unit 346 detects an air or other gas bubble in the coolant supply system 313, the sensor unit 346 transmits an electrical signal via transmission line 302 to the power generating source 28 and the flow-diverter apparatus 350. Sensor unit 346 and the power generating source 328 are similar to the sensor unit 46 and the power generating source 28, respectively, shown in FIG. 1 and further description thereof is omitted in the interests of brevity.

Coolant supply system 313 generally includes a coolant source 336, a first coolant path 319 leading from the coolant source 336 to the connection hub 322, and a second coolant path 320 leading from the connection hub 322 to the coolant source 336. In some embodiments, the first coolant path 319 includes a first fluid movement device 344 configured to move coolant fluid "F" through the first coolant path 319, and the second coolant path 320 includes a second fluid movement device 334 configured to move coolant fluid "F" through the second coolant path 320. Coolant source 336 stores coolant fluid "F", and may maintain coolant fluid "F" at a predetermined temperature. For example, the coolant source 336 may include a cooling unit (not shown) that cools the returning coolant fluid "F" from the antenna assembly 312.

Connection hub 322 may have a variety of suitable shapes, e.g., cylindrical, rectangular, etc. In some embodiments, the connection hub 322 includes a cable connector 379, an outlet fluid port 330 and an inlet fluid port 332. Connection hub 322 may include a three-branch luer type connector 372 having a middle branch 374 used to house the cable connector 379 and two outer branches 376 and 378 to house the outlet and inlet fluid ports 330 and 332, respectively. Connection hub 322 may be formed of any of a variety of materials, e.g., any suitable non-conductive conformal material. Examples of non-conductive conformal materials that may be suitable for forming the connection hub 322 include polyesters, polyimides, polyamides, polyamide-imides, polyetherimides, polyacrylates, polyethylene terephthalate, polyethylene, polypropylene, polyvinylidene chloride, polysiloxanes, combinations thereof and the like.

Connection hub 322 may be adapted to be connected in fluid communication with the sheath 338. In some embodiments, the sheath 338 is coupled to the connection hub 322 and the tip 123, thereby defining a chamber 337 around the feedline 110, the proximal radiating portion 140 and the distal radiating portion 105.

In some embodiments, the first coolant path 319 includes a coolant supply line 386 leading from the coolant source 336 to the inlet fluid port 332. First fluid movement device 344 may be disposed in fluid communication between the inlet fluid port 332 and the coolant source 336. In some embodiments, the second coolant path 320 includes a coolant return line 388 leading from the outlet fluid port 330 to the coolant source 336. Second fluid movement device 334 may be disposed in fluid communication between the outlet fluid port 330 and the coolant source 336. The positions of the first fluid movement device 344 and the second fluid movement device 334, e.g., in relation to the coolant source 336, may be varied from the configuration depicted in FIG. 3.

In some embodiments, a controller 351 associated with the flow-diverter apparatus 350 may actuate a fluid flow diverter 352 to divert coolant fluid "F" flow to a third coolant fluid path 321. Fluid flow diverter 352 may be any suitable device for selectively diverting the coolant fluid "F" flow. Third coolant fluid path 321 may lead from the flow-diverter apparatus 350 to a container 390. Controller 351 may include any type of computing device, computational circuit, or any type of processor or processing circuit capable of executing a series of instructions that are stored in a memory (not shown) of the controller 351.

In some embodiments, the flow-diverter apparatus 350 includes a valve (not shown) that includes a valve body and an electromechanical actuator operatively coupled to the valve body. Controller 351 may control fluid flow diverter 352 by activating the actuator, e.g., according to a predetermined valve control sequence. In some embodiments, a valve control sequence may involve moving the valve from a first position, in which coolant fluid "F" flows towards the connection hub 322, to a second position, in which the coolant fluid "F" having an air or other gas bubble entrained therein flows into the container 390, and returning to the first position, e.g., after a predetermined time interval, thereby re-establishing coolant fluid "F" flow towards the connection hub 322.

Hereinafter, methods of optical detection of interrupted fluid flow to an electrosurgical device, in accordance with the present disclosure, are described with reference to FIGS. 4 through 6. It is to be understood that the steps of the methods provided herein may be performed in combination and in a different order than presented herein without departing from the scope of the disclosure.

Figure 4:
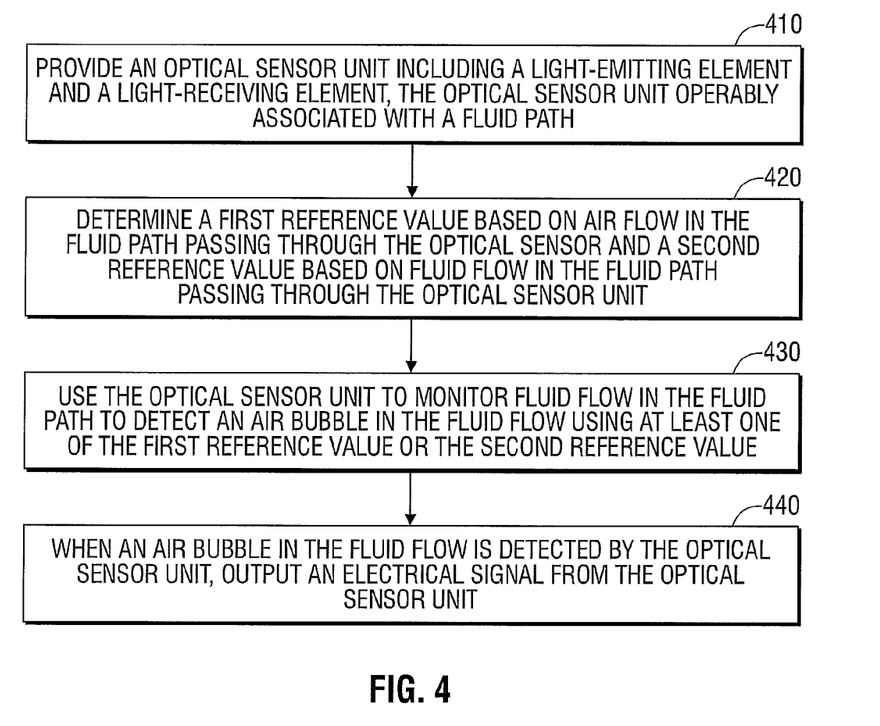
FIG. 4 is a flowchart illustrating a method of detecting an air bubble in a fluid flow according to an embodiment of the present disclosure.
Figure 5:
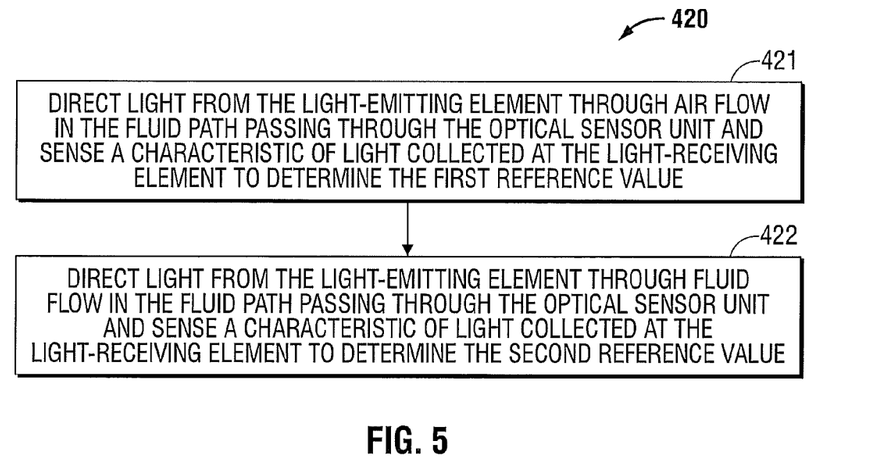
FIG. 5 is a flowchart illustrating an embodiment of the step of determining a first reference value and a second reference value of the method illustrated in FIG. 4 according to the present disclosure.

FIG. 4 is a flowchart illustrating a method of detecting a bubble in a fluid flow according to an embodiment of the present disclosure. In step 410, an optical sensor unit (e.g., 46 shown in FIG. 1) is provided that includes a light-emitting element (e.g., 43 shown in FIG. 1) and a light-receiving element (e.g., 40 shown in FIG. 1). The optical sensor unit is operably associated with a fluid path (e.g., 19 shown in FIG. 1). In some embodiments, the light emitting element and light-receiving element are disposed such that light directed from the light-emitting element passes through the fluid path to the light-receiving element during the fluid flow in the fluid path.

In step 420, a first reference value is determined based on an air flow in the fluid path passing through the optical sensor, and a second reference value is determined based on a fluid flow in the fluid path passing through the optical sensor unit. As illustrated in FIG. 5, step 420 may further include steps 421 and 422. In step 421, light from the light-emitting element is directed through the air flow in the fluid path passing through the optical sensor unit and a characteristic of light collected at the light-receiving element is sensed to determine the first reference value. In step 422, light from the light-emitting element is directed through the fluid flow in the fluid path passing through the optical sensor unit and a characteristic of light collected at the light-receiving element is sensed to determine the second reference value. In some embodiments, the sensed characteristic of light is an intensity of light collected at the light-receiving element. In other embodiments, the sensed characteristic of light is an absence of light incident on the light-receiving element.

In step 430, the optical sensor unit is used to monitor the fluid flow in the fluid path to detect an air bubble in the fluid flow using at least one of the first reference value or the second reference value. In sensor unit embodiments using signal intensity to detect an air bubble, the change in intensity of light collected at the light-receiving element is interpreted as indicator of the presence of an air bubble.

In step 440, when an air bubble in the fluid flow is detected by the optical sensor unit, an electrical signal is transmitted from the optical sensor unit. In some embodiments, when the sensor unit detects an air (or other gas) bubble in the coolant supply system, the sensor unit transmits an electrical signal to a power generating source (e.g., 28 shown in FIG. 1).

Figure 6:
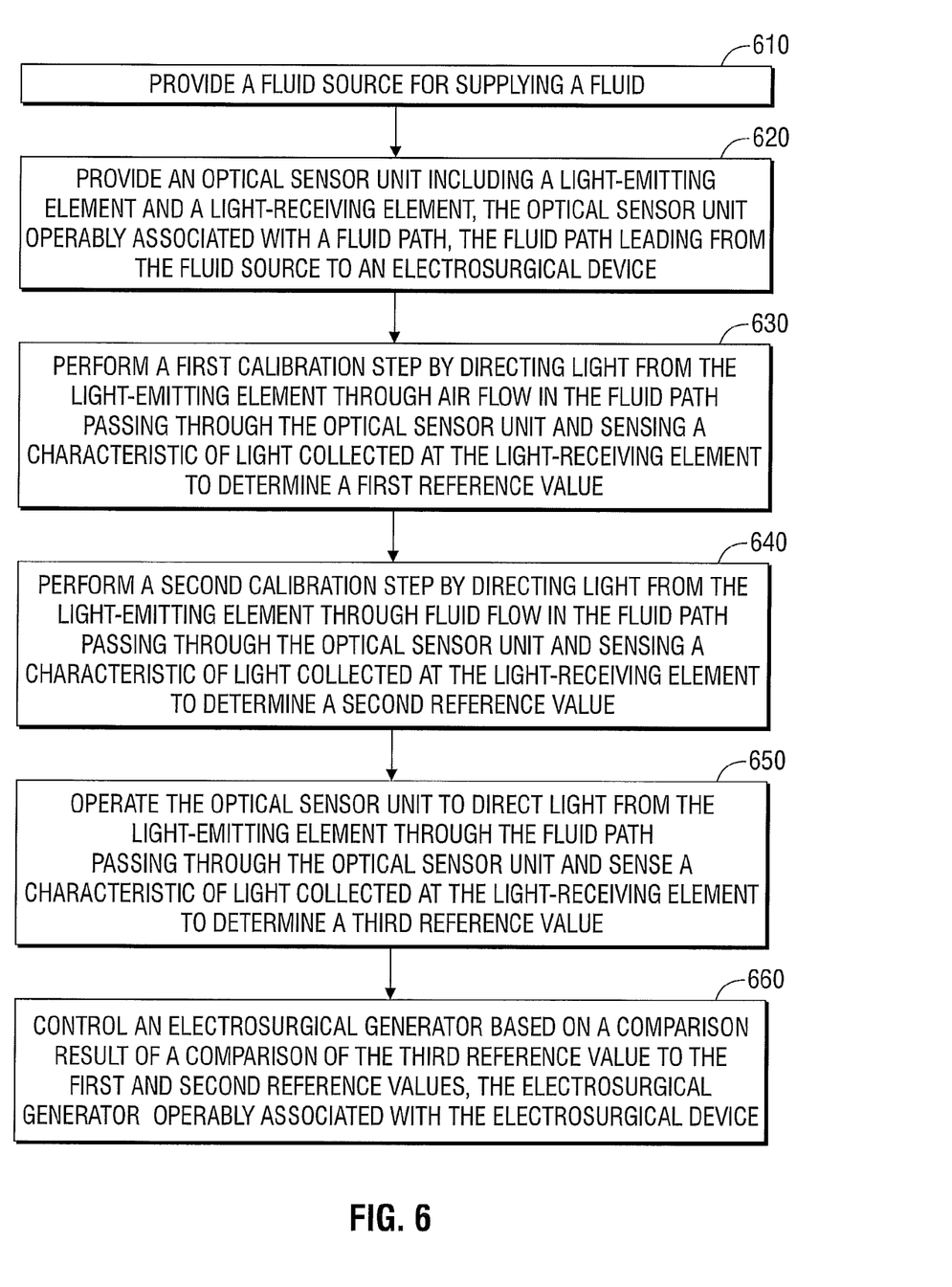
FIG. 6 is a flowchart illustrating a method of detecting an air bubble in a fluid flow according to another embodiment of the present disclosure.

FIG. 6 is a flowchart illustrating a method of detecting a bubble in a fluid flow according to an embodiment of the present disclosure. In step 610, a fluid source (e.g., 336 shown in FIG. 3) for supplying a fluid (e.g., "F" shown in FIG. 3) is provided. The fluid source may include any suitable source, e.g., a container of coolant or dielectric-buffering fluid.

In step 620, an optical sensor unit (e.g., 346 shown in FIG. 3) is provided that includes a light-emitting element (e.g., 43 shown in FIG. 3) and a light-receiving element (e.g., 40 shown in FIG. 3) The optical sensor unit is operably associated with a fluid path (e.g., 319 shown in FIG. 3), the fluid path leading from the fluid source to an electrosurgical device (e.g., 312 shown in FIG. 3) operably associated with an electrosurgical generator (e.g., 328 shown in FIG. 3).

In step 630, a first calibration step is performed by directing light from the light-emitting element through an air flow in the fluid path passing through the optical sensor unit and a characteristic of light collected at the light-receiving element is sensed to determine a first reference value.

In step 640, a second calibration step is performed by directing light from the light-emitting element through a fluid flow in the fluid path passing through the optical sensor unit and a characteristic of light collected at the light-receiving element is sensed to determine a second reference value.

In step 650, the optical sensor unit is operated to direct light from the light-emitting element through the fluid flow in the fluid path passing through the optical sensor unit and a characteristic of light collected at the light-receiving element is sensed to determine a third reference value.

In step 660, an electrosurgical generator, which may be used to activate the electrosurgical device, is controlled based on a comparison result of a comparison of the third reference value to the first reference value and the second reference value. In some embodiments, the optical sensor unit is electrically coupled to the electrosurgical generator. Based on the comparison result, the optical sensor unit may output an electrical signal to the electrosurgical generator and, in response thereto, the power output of the electrosurgical generator may be reduced, e.g., for a predetermined time interval or until a manual reset switch is actuated. In some embodiments, the optical sensor unit outputs an electrical signal when the third reference value is determined to be substantially equal to the first reference value.

In some embodiments, the fluid flow may be diverted by a flow-diverter apparatus (e.g., 350 shown in FIG. 3) to a different fluid path (e.g., 321 shown in FIG. 3) for a predetermined period of time based on the comparison result. The predetermined period of time may be a period of time to allow for the air bubble to pass out of the fluid path (e.g., 319 shown in FIG. 3) that leads to the electrosurgical device and, instead, into a different fluid path (e.g., 321 shown in FIG. 3), e.g., leading to a container (e.g., 390 shown in FIG. 3). In some embodiments, the electrosurgical system (e.g., 1000 shown in FIG. 3) controls electrical characteristics of the electrosurgical generator to deactivate the electrosurgical device (e.g., 312 shown in FIG. 3) during the predetermined time period.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A method of detecting an air bubble in a fluid flow, comprising the steps of:
   providing an optical sensor unit including a light-emitting element and a light-receiving element, the optical sensor unit operably associated with a fluid path;
   determining a first reference value based on air flow in the fluid path passing through the optical sensor unit;
   determining a second reference value based on fluid flow in the fluid path passing through the optical sensor unit;
   using the optical sensor unit to monitor fluid flow in the fluid path to detect an air bubble in the fluid flow using at least one of the first reference value or the second reference value;
   when an air bubble in the fluid flow is detected by the optical sensor unit, outputting an electrical signal from the optical sensor unit to a flow diverter apparatus and an electrosurgical energy source in response to detection of the air bubble in the fluid flow; and
   adjusting energy output of the electrosurgical energy source in response to the electrical signal from the optical sensor unit.

2. The method of detecting an air bubble in a fluid flow in accordance with claim 1, wherein the light emitting element and light-receiving element are disposed such that light directed from the light-emitting element passes through the fluid path to the light-receiving element.

3. The method of detecting an air bubble in a fluid flow in accordance with claim 1, wherein determining the first reference value based on air flow in the fluid path passing through the optical sensor unit further includes the step of:
   directing light from the light-emitting element through air flow in the fluid path passing through the optical sensor unit and sensing a characteristic of light collected at the light-receiving element to determine the first reference value.

4. The method of detecting an air bubble in a fluid flow in accordance with claim 1, wherein determining the second reference value based on fluid flow in the fluid path passing through the optical sensor unit further includes the step of:
   directing light from the light-emitting element through fluid flow in the fluid path passing through the optical sensor unit and sensing a characteristic of light collected at the light-receiving element to determine the second reference value.

5. The method of detecting an air bubble in a fluid flow in accordance with claim 1, further including the step of:
   providing a container for collecting fluid diverted by the flow-diverter apparatus.

6. The method of detecting an air bubble in a fluid flow in accordance with claim 5, further including the step of:
   actuating the flow-diverter apparatus to divert fluid flow to the container in response to the electrical signal from the optical sensor unit.

7. A method of detecting an air bubble in a fluid flow, comprising the steps of:
   providing a fluid source for supplying a fluid;
   providing an optical sensor unit including a light-emitting element and a light-receiving element, the optical sensor unit operably associated with a first fluid path, the first fluid path leading from the fluid source to an electrosurgical device;
   performing a first calibration step by directing light from the light-emitting element through air flow in the first fluid path passing through the optical sensor unit and sensing a characteristic of light collected at the light-receiving element to determine a first reference value;
   performing a second calibration step by directing light from the light-emitting element through fluid flow in the first fluid path passing through the optical sensor unit and sensing a characteristic of light collected at the light-receiving element to determine a second reference value;
   operating the optical sensor unit to direct light from the light-emitting element through the first fluid path passing through the optical sensor unit and to sense a characteristic of light collected at the light-receiving element to determine a third reference value;
   when an air bubble in the fluid flow is detected by the optical sensor unit, outputting an electrical signal from the optical sensor unit to a flow diverter apparatus and an electrosurgical energy source in response to detection of the air bubble in the fluid flow; and
   adjusting energy output of the electrosurgical energy source in response to the electrical signal from the optical sensor unit.

8. The method of detecting an air bubble in fluid flow in accordance with claim 7, further comprising: outputting the electrical signal when the third reference value is determined to be substantially equal to the first reference value.

9. The method of detecting an air bubble in a fluid flow in accordance with claim 7, further including the step of:
   diverting the fluid flow to a second fluid path for a predetermined period of time based on the electrical signal from the optical sensor unit.

10. A method of detecting an air bubble in a fluid flow, comprising:
    monitoring fluid flow in a fluid path to detect an air bubble in the fluid flow at an optical sensor operably associated with the fluid path, the optical sensor including a light-emitting element and a light-receiving element;
    outputting an electrical signal from the optical sensor to a flow diverter apparatus in response to a detection of an air bubble in the fluid flow; diverting the fluid flow at the flow diverter to a container in response to the electrical signal from the optical sensor; and
    adjusting energy output of an electrosurgical energy source in response to the electrical signal from the optical sensor.

* * * * *